(12) United States Patent
Dimsdale et al.

(10) Patent No.: US 7,187,823 B2
(45) Date of Patent: Mar. 6, 2007

(54) CONTACT-FREE SLIP RING FOR SURVEY INSTRUMENTATION

(75) Inventors: Jerry Dimsdale, Oakland, CA (US); Joseph N. West, Petaluma, CA (US)

(73) Assignee: Leica Geosystems HDS LLC, San Ramon, CA (US)

( * ) Notice: Subject to any disclaimer, the term of this patent is extended or adjusted under 35 U.S.C. 154(b) by 200 days.

(21) Appl. No.: 11/081,976

(22) Filed: Mar. 16, 2005

(65) Prior Publication Data

US 2005/0279914 A1    Dec. 22, 2005

Related U.S. Application Data

(60) Provisional application No. 60/553,860, filed on Mar. 16, 2004.

(51) Int. Cl.
  *G02B 6/26*   (2006.01)
  *G02B 6/42*   (2006.01)
(52) U.S. Cl. .................. 385/26; 385/134; 385/139
(58) Field of Classification Search ............... 385/26
  See application file for complete search history.

(56) References Cited

U.S. PATENT DOCUMENTS

| | | | |
|---|---|---|---|
| 5,691,687 A | 11/1997 | Kumagai et al. | 336/120 |
| 5,988,862 A | 11/1999 | Kacyra et al. | 703/6 |
| 6,420,698 B1 | 7/2002 | Dimsdale | 250/234 |
| 6,452,668 B1 | 9/2002 | Pratt | 356/141.4 |
| 6,593,582 B2 | 7/2003 | Lee et al. | 250/458.1 |
| 6,604,068 B1 | 8/2003 | Bukowski et al. | 703/22 |
| 6,630,993 B1 | 10/2003 | Hedges et al. | 356/141.4 |
| 6,633,290 B1 | 10/2003 | Kung et al. | 345/423 |
| 6,804,380 B1 | 10/2004 | Ioannou et al. | 382/103 |
| 6,870,608 B2 | 3/2005 | Detweiler et al. | 356/141.1 |
| 6,898,346 B2 * | 5/2005 | Mercey et al. | 385/26 |

OTHER PUBLICATIONS

A. Esser et al., "Contactless High Speed Signal Transmission Integrated in a Compact Rotatable Power Transformer," *The European Power Electronics Association* (1993), pp. 409-414.
R.D. Lorenz, "Robotics and Automation Applications of Drives and Converters," *Proceedings of the IEEE*, vol. 89, No. 6, Jun. 2001, pp. 951-962.
G. Roberts et al., "Design and Evaluation of the Power and Data Contactless Transfer Device," *IEEE* (1997), pp. 523-533.
G. Roberts, A Contactless Transfer Device for Power and Data, *Proceedings IEEE—Aerospace Applications Conference* (1996), pp. 333-345.

* cited by examiner

*Primary Examiner*—Frank G. Font
*Assistant Examiner*—Mary El-Shammaa
(74) *Attorney, Agent, or Firm*—Stallman & Pollock LLP

(57) ABSTRACT

A contact free rotary transformer assembly can be used to transfer power and information between a stationary portion and a rotatable portion of a laser scanning device. The rotary transformer can consist of a pair of substantially parallel ferrite rings, each having disposed therein a coil for passing AC current. The assembly can use an optical fiber positioned near a rotational axis of the transformer to transfer optical information between the stationary and rotary portions. The optical fiber can include two portions connected by a rotational connection in order to allow the portions to rotate with respect to one another while maintaining the light path.

14 Claims, 7 Drawing Sheets

US 7,187,823 B2

CONTACT-FREE SLIP RING FOR SURVEY INSTRUMENTATION

CLAIM OF PRIORITY

This application claims priority to U.S. Provisional Patent Application No. 60/553,860, entitled "LASER SCANNING SYSTEM," filed Mar. 16, 2004, which is hereby incorporated herein by reference.

TECHNICAL FIELD OF THE INVENTION

The present invention relates to surveying devices and apparatus, such as laser scanning survey devices.

BACKGROUND

The acquisition of data and subsequent generation of computer models for real-world objects is of interest in many industries, for applications including architecture, physical plant design, entertainment applications (e.g., in movies and games), surveying, manufacturing quality control, medical imaging, and construction, as well as cartography and geography applications. In order to obtain accurate models of an object, as well as the area in which that object exists in the real world, it is necessary to take accurate measurements or samplings of surfaces that make up the object and any elements of the surrounding area. Historically, this sampling was carried out by surveyors, photogrammetrists, or technicians using techniques that provided samples at the rate of tens or hundreds per hour at most. Since the amount of data was relatively small, the data was easily dealt with in standard, off-the-shelf CAD programs or other modeling software.

Recent advances in scanning technology, such as technologies utilizing LIDAR scanning, have resulted in the ability to collect billions of point samples on physical surfaces, over large areas, in a matter of hours. In a LIDAR process, a laser beam scans across a view that encompasses the structure of interest. The scanning device measures a large number of points that lie on surfaces visible in the scene. Each scan point has a measured location in 3D space, to within some measurement error, that typically is recorded relative to a point (x,y,z) in the local coordinate system of the scanner. The resulting collection of points is often referred to as one or more point clouds, where each point cloud can include points that lie on many different surfaces in the scanned view. LIDAR systems are described, for example, in U.S. Pat. No. 5,988,862, filed Apr. 24, 1996, entitled "INTEGRATED SYSTEM FOR QUICKLY AND ACCURATELY IMAGING AND MODELING THREE DIMENSIONAL OBJECTS," which is hereby incorporated herein by reference.

An exemplary surveying system 100 shown in FIG. 1 utilizes a Field Digital Vision (FDV) module 102 that includes a scanning device for scanning an object 104, such as a building of a piece of machinery. The scanning device also can sense the position in three-dimensional space of selected points on the surface of the object 104. The FDV module 102 generates a point cloud 106 that represents the detected positions of the selected points. The point cloud 106 also can represent other attributes of the detected positions, such as reflectivity, surface color, and texture, where desired.

A control and processing station 108 interacts with the FDV 102 to provide control and targeting functions for the scanning sensor. In addition, the processing and control station 108 can utilize software to analyze groups of points in the point cloud 106 to generate a model of the object of interest 104. A user interface 116 allows a user to interact with the system, such as to view a two-dimensional (2D) representation of the three-dimensional (3D) point cloud, or to select a portion of that object to be viewed in higher detail as discussed elsewhere herein. The processing station can include any appropriate components, such as standard computer and/or processing components. The processing station also can have computer code in resident memory, on a local hard drive, or in a removable drive or other memory device, which can be programmed to the processing station or obtained from a computer program product such as a CD-ROM or download signal. The computer code can include instructions for interacting with the FDV and/or a user, and can include instructions for undertaking and completing any modeling and/or scanning process discussed, described, or suggested herein.

The FDV 102 can include an optical transceiver 110 capable of scanning points of the object 104, and that generates a data signal that precisely represents the position in 3D space of each scanned point. The data signal for the groups of scanned points can collectively constitute the point cloud 106. In addition, a video system 112 can be provided, which in one embodiment includes both wide angle and narrow angle CCD cameras. The wide angle CCD camera can acquire a video image of the object 104 and provides to the control and processing station 108, through a control/interface module 114, a signal that represents the acquired video image.

The acquired video image can be displayed to a user through a user interface 116 of the control and processing station 108. Through the user interface 116, the user can select a portion of the image containing an object to be scanned. In response to user input, the control and processing station can provide a scanning control signal to the transceiver 110 for controlling the portion of the surface of the object that should be scanned by the transceiver. More particularly, the scanning control signal can be used to control an accurate and repeatable beam steering mechanism that steers a beam or pulse of the transceiver 110. The narrow angle CCD camera of the video system 112 can capture the intensity returned from each scan impingement point, along with any desired texture and color information, and can provide this captured information to the control and processing station 108. The control and processing station can include a data processing system (e.g., a notebook computer or a graphics workstation) having special purpose software that, when executed, instructs the data processing system to perform the FDV 102 control and targeting functions, and also to perform the model generation functions discussed elsewhere herein. Once the object has been scanned and the data transferred to the control and processing station, the data and/or instructions relating to the data can be displayed to the user.

FIG. 2 shows a block diagram of an optical transceiver 200 of the FDV of the prior art. The optical transceiver 200 transmits an optical pulse to a spot on an object (or structure) being scanned, and receives back an optical pulse reflected from the object. Given the constant speed of light, the optical transceiver calibrates the distance to the spot on the target. A laser 202 in this example is used to generate an optical pulse, which typically lasts less than 250 psec, in response to a command provided from a laser controller 204. The laser 202 produces the pulse, at a wavelength such as about 532 nm, within about 100–300 microseconds after receiving a command signal. The command signal emanates from a digital signal processor that provides central control of real time events. The time delay is a function of variables such as laser age, recent laser history, and environmental/operating conditions. Power and control signals can be provided to the transceiver from a set of scanning control and power components 220. Another set of components 222 can be used that includes additional power electronics, as well as interface components for interfacing with a user, other internal or external devices, and/or processing equipment.

The output of the laser 202 is transmitted through a beam expander 206 that is focused to adjust the size of a light spot that will eventually impinge upon a point on the object being scanned. The focused optical pulse then is transmitted through a duplexer 208, which is an optical system for aligning the outgoing optical path with the incoming optical path. The duplexer 208 directs a significant first portion of the light energy of the outgoing optical pulse to a spot on the object via a scanner. A second but much smaller portion of the light energy of the outgoing optical pulse is directed to a receiver telescope 212. The portion of the outgoing optical pulse that propagates to the object impinges on a spot on the object, and some of the energy of the optical pulse is reflected off the object in a direction back to the duplexer 208. The scanner (not shown) typically includes a beam steering unit, or beam deflection unit, that utilizes one or more mirrors or other optical elements for directing the output pulse. In order to direct the output pulse to scan in two dimensions, a pair of mirrors can be used to direct the pulse along two linear axes. This can include a first mirror device and a second mirror device, each capable of rotating relative to a rotational axis. In one example, a first mirror rotates parallel to a rotational axis of the beam steering unit. A drive motor functions to rotate the second mirror about a second rotational axis, which typically is orthogonal to the rotational axis of the beam steering unit. The rotation along the two axes allows for direction of the beam along a two-dimensional path, such as a raster pattern. Light reflected from the object can be received by the scanner and directed by the first and second mirror devices to the optical transceiver 200.

The returning optical pulse is directed by the duplexer 208 to the receiver telescope 212, which focuses the received energy onto a detector 214. The detector 214 converts the received optical pulse energy into electrical energy. The output of the detector is a series of electrical pulses, the first (generated by the detector in response to the small portion of the transmitted pulse not directed toward the object) occurring at a short fixed time (i.e., fixed by the length of the optical path through the beam expander, duplexer, and receiver telescope) and the second occurring as light energy returns from the object. Both the second, small portion of the transmitted pulse and the return optical pulse reflected from the spot on the object are provided to the timing circuit 216, which calculates the time of flight to the spot on the object. The range to the spot on the object can then be readily calculated from the calculated time of flight.

In order to allow for rotation of the beam deflection unit(s) in the scanner of this example, it is necessary to have a rotary connection allowing at least a portion of each beam deflection unit, such as the first and/or second mirror devices, to rotate relative to the rest of the FDV. Surveying instrumentation can have any of a number of points that require precise rotary components to deliver high angular precision, such as for deflecting light beams and/or adjusting viewing optics. If the rotary portions are instrumented, for example, both information and power may need to flow through this rotary connection. Existing survey instrumentation typically solves this problem through use of electromechanical slip rings. Electro-mechanical slip rings consist of one or more rings and a number of brushes, both the ring(s) and brushes being made of conductive material. The rings or brushes are connected to the stationary unit, with the other part being connected to a rotary portion. An electrical current is applied from the stationary side, such that current passes through the mechanical contact between the ring and brushes. This mechanical contact can be undesirable, as a small dust particle or mechanical imperfection can lead to occasional breaks in the mechanical contact and thus a break in current flow. Breaks in current can lead to increased levels of noise in the system. Another problem is that these mechanical connections have the potential for sparking, which can be a severe detriment in explosive environments. These mechanical connections also experience frictional effects, which can affect the angular precision of the rotation.

DETAILED DESCRIPTION

Systems and methods in accordance with embodiments of the present invention can overcome deficiencies in existing scanning systems by changing the way in which power and information are transmitted between rotary and stationary portions of a system. In at least one embodiment, power and information can be transmitted through a contact-free rotary joint without any cables or sliding contacts. This rotary joint can consist of a combination of electrically—and optically-coupled transmission paths. A rotary transformer is used for power transmission, avoiding problems with the typical slip ring approach in existing systems. The basic principals of rotary transformers are known in the art and will not be discussed in detail herein, as rotary transformers commonly are applied in systems such as videocassette recorders for the purpose of transmitting data and power. The information channels that typically take the form of cabling can be replaced with at least one light path using an optical data link. The basic principals of optical data links are known in the art and will not be discussed herein, as such data links are used in applications such as satellite gyroscopic systems. Typical off-the-shelf optical links have integral bearings, however, which can be undesirable for many survey instruments.

Figure 3A:
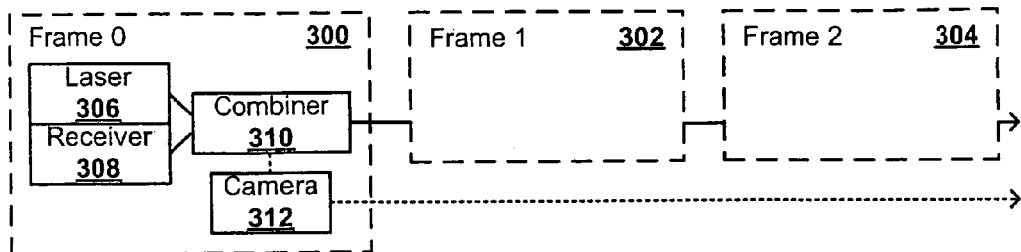
FIGS. 3(*a*)–(*c*) show arrangements of the components of FIG. 2 that can be used in accordance with embodiments of the present invention.

The use of rotary joint assemblies as described herein can not only allow for the transmission of power and/or information between portions of a scanning device, but also can allow for components to be moved to various regions of the device. For instance, a relatively traditional scanner configuration is shown in FIG. 3(a). This configuration includes what will be referred to herein as three frames of reference. One frame of reference (Frame 0 300) can be a stationary frame that does not rotate relative to an object being scanned. This can be, for example, a frame of reference that includes a rigid stand holding the scanning instrument in place. In typical scanners, the laser 306, receiver 308, combiner 310, and camera(s) 312 are positioned in the stationary frame 300. The camera 312 can capture light that passes through the combiner 310, or can be a wide angle camera that captures reflected light directly from the object being scanned.

Output pulses from the laser, and pulses reflected back to the receiver, can pass through a scanner including a first rotational axis and a second rotational axis, in order to scan the object in two dimensions as discussed above. For each rotational axis, another frame of reference is created relative to the object being scanned. For instance, the rotation about a first axis creates Frame 1 302, which can include components that rotate relative to Frame 0 300. Frame 1 can include a first mirror device or beam deflecting unit for deflecting the optical pulses in a first dimension. A second rotation about a second axis creates Frame 2 304, which can include other components that rotate relative to both Frame 0 and Frame 1. Frame 2 can include a second mirror device or beam deflecting unit for deflecting the optical pulses in a second dimension, such as a dimension orthogonal to the first dimension. This arrangement allows the majority of the laser components to be stationary, while two stages of a scanner or beam deflecting device(s) can rotate to allow appropriate deflection of the optical pulses. Because there may be no need to transfer data and/or power to Frame 1 and Frame 2 in this arrangement, there may be no need to use rotary joint assemblies as described herein. It can be useful, however, to use a rotary joint assembly between Frame 0 and Frame 1, and/or between Frame 1 and Frame 2, in order to allow for a precise rotation of the respective frames. Further, there may be motor devices in at least one of those frames that require power transmission. In such case, rotary joint assemblies as described herein can be useful between frames.

Figure 1:
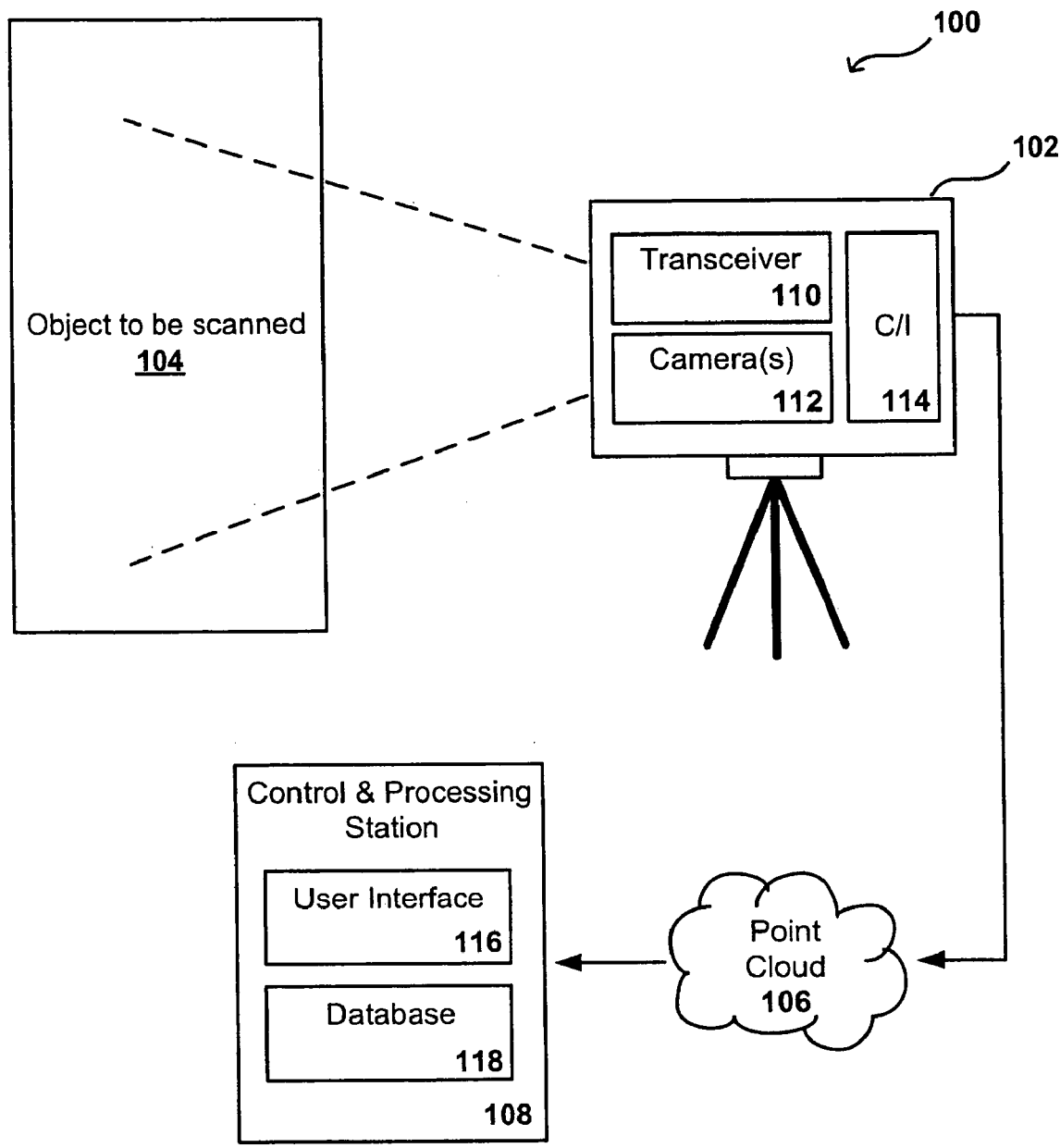
FIG. 1 is a diagram of a scanning survey system that can be used in accordance with one embodiment of the present invention.
Figure 2:
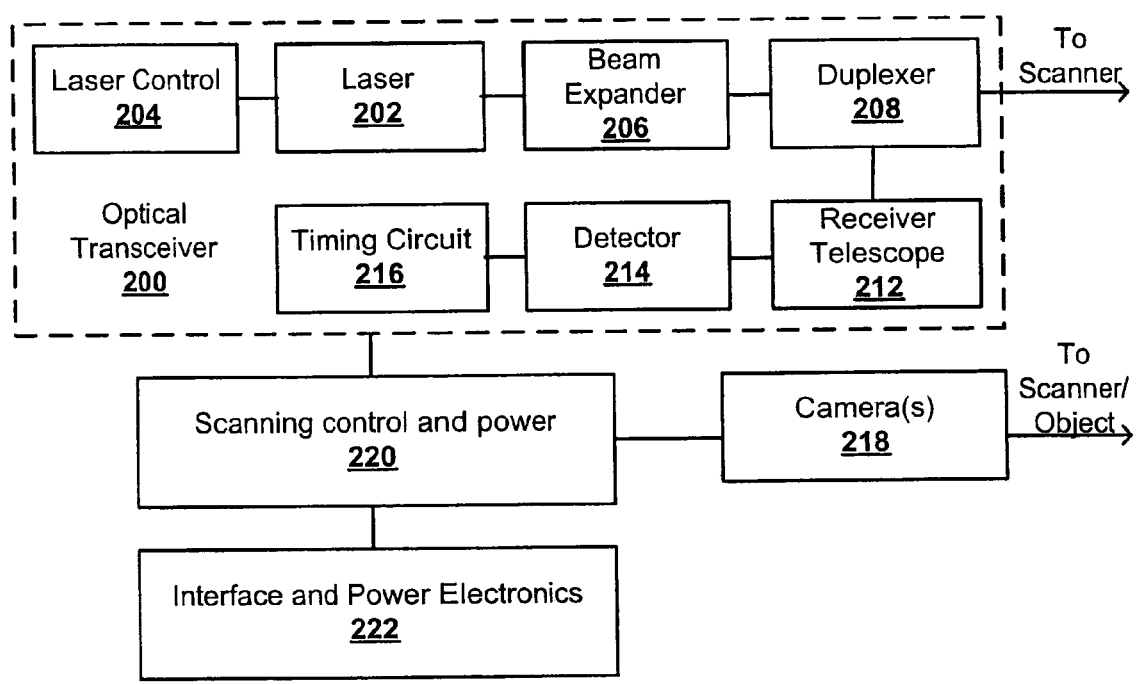
FIG. 2 is a diagram showing components that can be used with the survey system of FIG. 1.
Figure 3B:
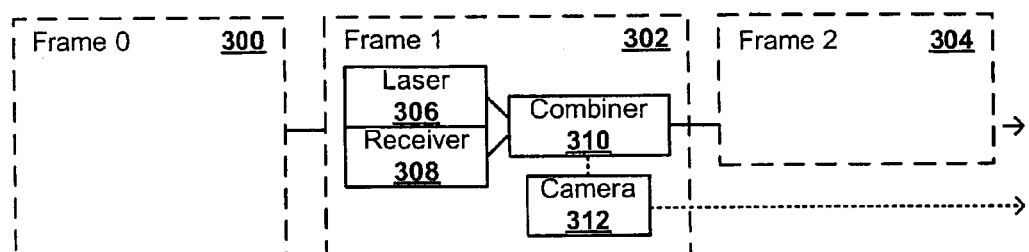

Another arrangement of survey instrument components is shown in FIG. 3(b). In this example, the laser 306, receiver 308, combiner 310, and camera 312 can be placed in Frame 1 302, which is capable of rotation with respect to Frame 0 300. In this case, power is transferred from the components of the stationary frame, such as the set of interface and power electronics discussed with respect to FIG. 2, to the surveying components in rotatable Frame 1. Further, the data captured by the components in Frame 1 is transmitted back to the components in the stationary frame. In order to allow for a precise rotation of Frame 1, it can be desirable to avoid the use of cabling between the Frame 1 and Frame 0 components, which can provide a source of tension or stress that can affect the rotational accuracy. As such, it can be desirable to use a rotary joint assembly as described herein to transmit power and/or information between Frame 0 and Frame 1. A rotary joint assembly also can be used between Frame 1 and Frame 2, as described with respect to FIG. 3(a).

Figure 3C:
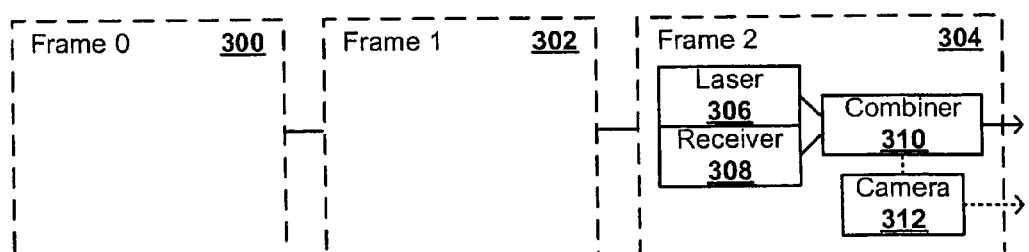

Yet another arrangement is shown in FIG. 3(c). In this arrangement, the components are positioned in Frame 2 304, which can rotate relative to both Frame 0 300 and Frame 1 302. As such, it can be desirable to use a rotary joint assembly as described herein to transmit power and/or information between Frame 0 and Frame 1, as well as between Frame 1 and Frame 2. Other arrangements are also possible, wherein various components are split over the frames, such as a laser being positioned in Frame 2 and a receiver positioned in Frame 1. Rotary joint assemblies can be used anywhere in these arrangements where a rotary joint is needed, and it is desirable to have a precise rotation and/or to pass power and/or information.

Figure 4:
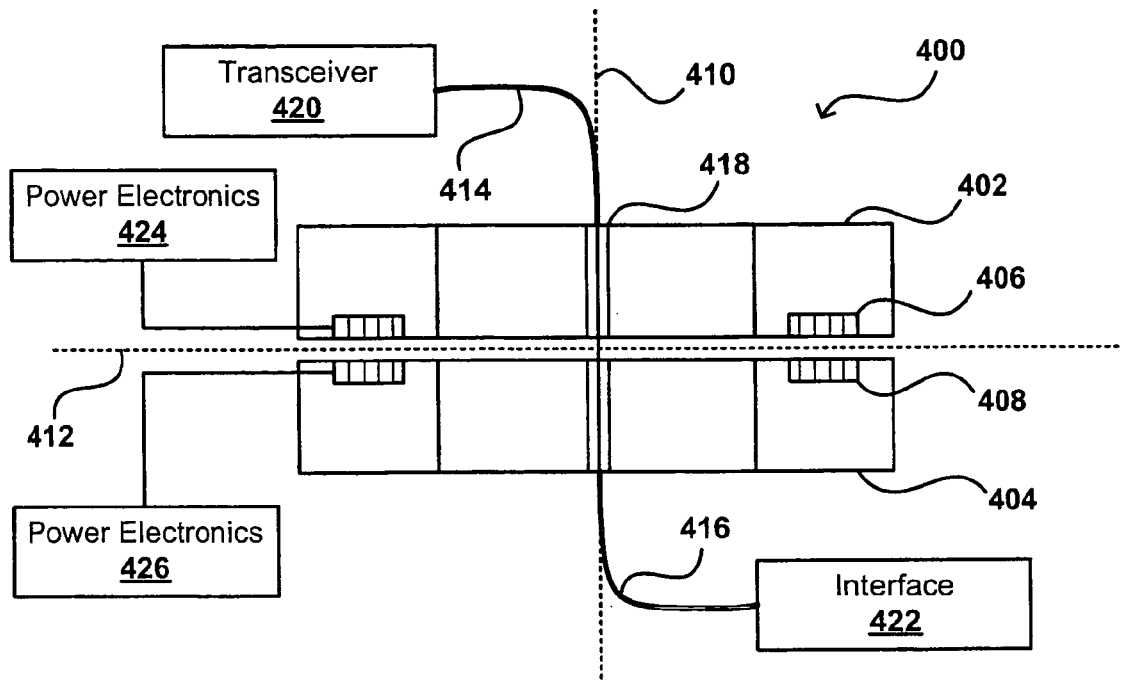
FIG. 4 is a diagram of a first contact free slip ring assembly that can be used with the system of FIG. 1.

FIG. 4 shows an exemplary rotary joint assembly 400 that can be used in accordance with the arrangements of FIG. 3 and other embodiments of the present invention. This assembly 400 utilizes a pair of magnetically coupled wire coils 406, 408 forming a rotary transformer that is substantially symmetric about a rotary axis 410. Line 412 is used to illustrate the separation between stationary components and rotary components in this example. The rotary transformer includes a pair of identical ring-shaped cores 402, 404, for housing the coils, capable of inductively coupling power therebetween. The cores can be formed of any appropriate material, such as ferrite. The ferrite cores each can include a groove in the adjacent sides of the cores for housing coils of wire. By having the coils face each other in the ferrite cores, the coupling between the two coils of wire is increased relative to a case without the ferrite cores. Further, the ferromagnetic cores cause the coils to be magnetically isolated from external fields.

Power can be applied to, for example, a coil mounted inside the bottom ferrite ring core 404. The magnetic field lines can pass largely through the low reluctance path of the ferrite material into the matching ring core 402 through the gap between the cores. A voltage will be induced in the coil mounted in the top ferrite core 402, allowing power to be transferred between the coils of the cores.

Such a rotary transformer can be used to couple AC electrical power between scanning components, such as by passing power between a first set of power electronics 424 and a second set of power electronics 426, wherein one set of power electronics is capable of rotating relative to the other set. The electrical power coupling can be provided by the inductive energy transfer capability of the rotary transformer assembly 400. Unlike conventional slip rings, this rotary transformer assembly does not make mechanical contact between the ring core elements, such that problems with intermittent contact and sparking can be avoided. The coil in each ring core can have a predetermined number of wrapped wires or a number of wrappings of a single wire. The number of wires and/or wrappings can depend upon the gauge of the wire used. Each wrapped wire of a primary coil can have first and second ends connected to a component such as a transceiver or rectifier.

The transmitting power electronics 426 can include a source of AC power. The voltages that can be used with the rotary transformer can depend upon the characteristics of the wrapped wire in the adjacent grooves of the ring cores. Electronics providing power on one side of the rotary joint can include a rectifier and at least one DC voltage regulator, providing power and voltage to the various components on the other side of the rotary transformer. The electronics can convert DC power at a specified voltage and current to AC power at a specified voltage and current to be drive the rotary transformer, and can allow an AC current to be passed through the rotary transformer to power electronic, which can convert the AC power into a DC power. The rotary connection can be constructed with integral shielding, to reduce susceptibility to interference from outside optical and/or electromagnetic signals. As shown in FIGS. 6(a)–6(e), a ring core 404 can include a channel 600 that allows space for power cabling or wiring 602 to connect the wire coil in the ring groove 408 to the appropriate components of the system, such as a rectifier for converting between DC and AC power. The channel is shown in detail in FIG. 6(e), with a depth relation relative to the groove shown in FIG. 6(d). The channel typically will be deeper than the groove to allow an end of the coil wire to be passed underneath the coil, or away from the adjacent coil, to connect one end of the coil to the appropriate device.

In order to allow an optical signal to be passed between a data interface 422 of a stationary portion of the FDV and an optical transceiver 420 in a rotary frame, for example, which can be rotatable with respect to each other, an optical link can be placed substantially on axis with the rotational axis 410 of the ring transformer assembly. The optical link can use standard wave-division multiplexed optical transceivers. Intervening optics can be used to focus the resulting light beams. At least one transceiver can be a bi-directional optical transceiver that coverts between digital signals and light pulses. A wave division multiplexed transceiver can be used, although a single light wavelength can be used by separating the light paths. The input/output of this transceiver can be coupled into a single optical fiber 414, which enters the central opening 418 in the contact free slip ring assembly. The fiber can be a single, continuous fiber, or can consist of a first fiber portion 414 and a second fiber portion 416. The first and second fiber portions can connect through a rotary connection, as will be described with respect to FIG. 7, allowing the portions of the fiber to rotate with respect to one another while allowing for a common light path. The fiber can be coupled to a number of intervening optics (not shown) in order to point the beam along the axis of rotation of the system, or other light path, as well as to receive and transmit light passed along the fiber. The system can be set up such that light propagates in one direction through the fiber at a first wavelength, and in the opposite direction at a second wavelength, such that light traveling in opposing directions with not interfere. These wavelengths can be, for example, around 1300 nm and 1500 nm.

FIG. 7 shows an example of a first fiber portion 700 and a second fiber portion 706. As can be seen, each portion contains a connector 702, 708 selected to connect to the appropriate device, such as a transceiver. Each portion can be designed to contain an optical fiber, such as an optical fiber in the range of 124–400 microns in diameter, and can have an optically insulating coating as known in the art. Each portion can include a strain relief component at the appropriate connection points. As shown, the first portion 702 can include an accepting connection member 704, which can include a central opening along the light path to receive a portion of an optical fiber. The second portion can include a projecting connection member 710, shaped to be received by the accepting connection member 704. The connection members can be connected to allow rotation of one of the fiber portions at the connection point relative to the other fiber portion. The placement of the optical fiber at the central axis of each connection member also allows for a consistent light path, regardless of the rotation of the fibers. Such a connection allows for an unlimited range of rotation, without the need to worry about tangling and/or excessive bending of the fiber. The connection members can be made out of any appropriate material, and can be polished in order to reduce the likelihood of frictional effects. The connection members also can be lubricated using a lubricant that is acceptable for optical applications.

Other means of transferring data or information between a rotary optical transceiver and a stationary data interface, for example, include transmitting data via an inductive path through the rotary transformer. Methods for transmitting data through primary and secondary coils are known, such as are described in U.S. Pat. No. 5,691,687, entitled "Contactless Magnetic Slip Ring," which is hereby incorporated herein by reference. The data path also can be multiplexed to carry scan signals in order to move portions of the transceiver to other sections of the scanning device.

Figure 5:
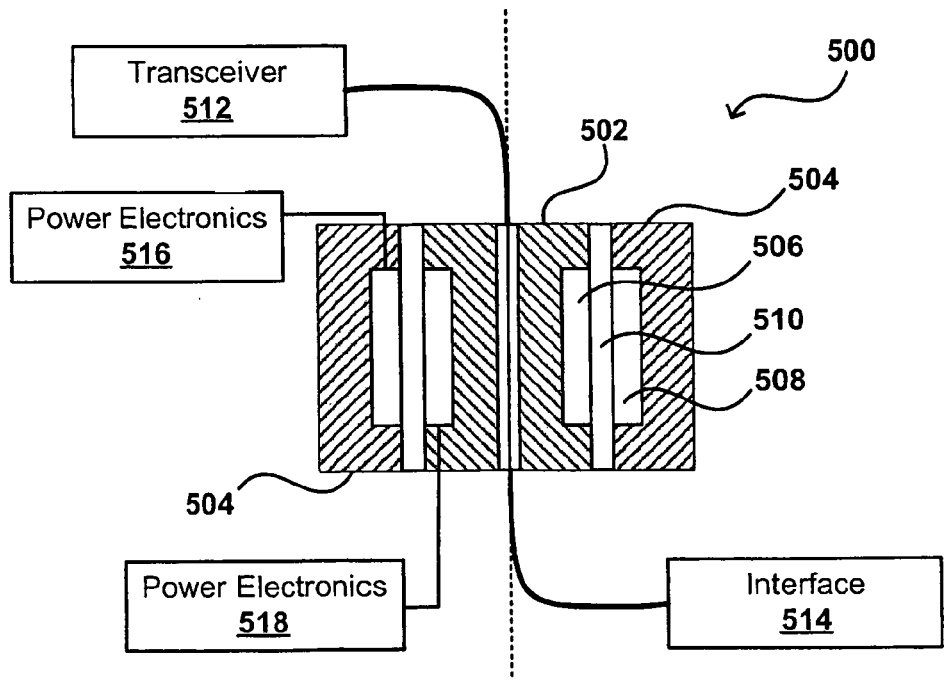
FIG. 5 is a diagram of a second contact free slip ring assembly that can be used with the system of FIG. 1.
Figure 6A:
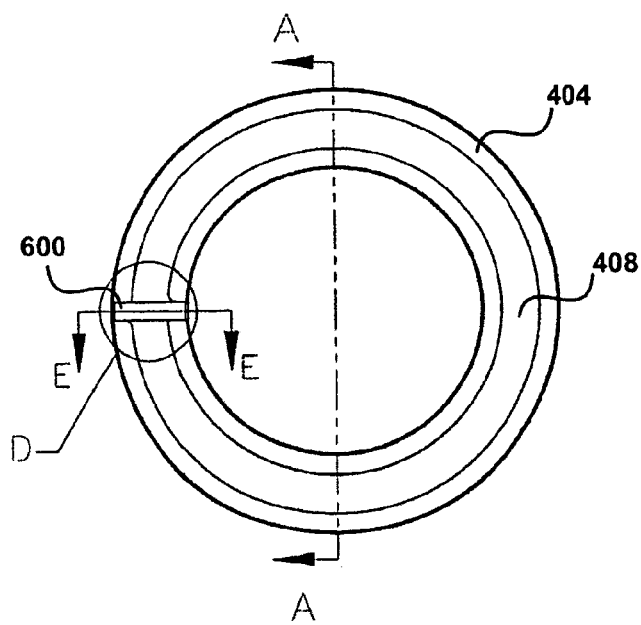
FIGS. 6(*a*)–(*e*) show views of a component of the slip ring of FIG. 4.
Figure 6C:
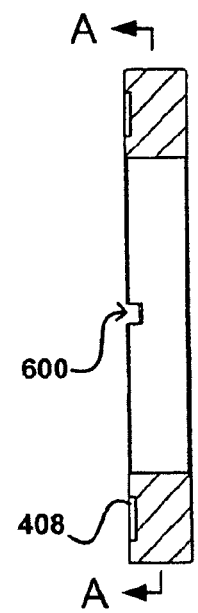
Figure 6D:
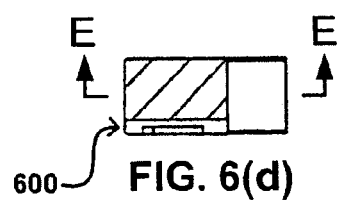
Figure 6E:
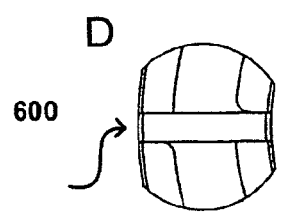
Figure 6B:
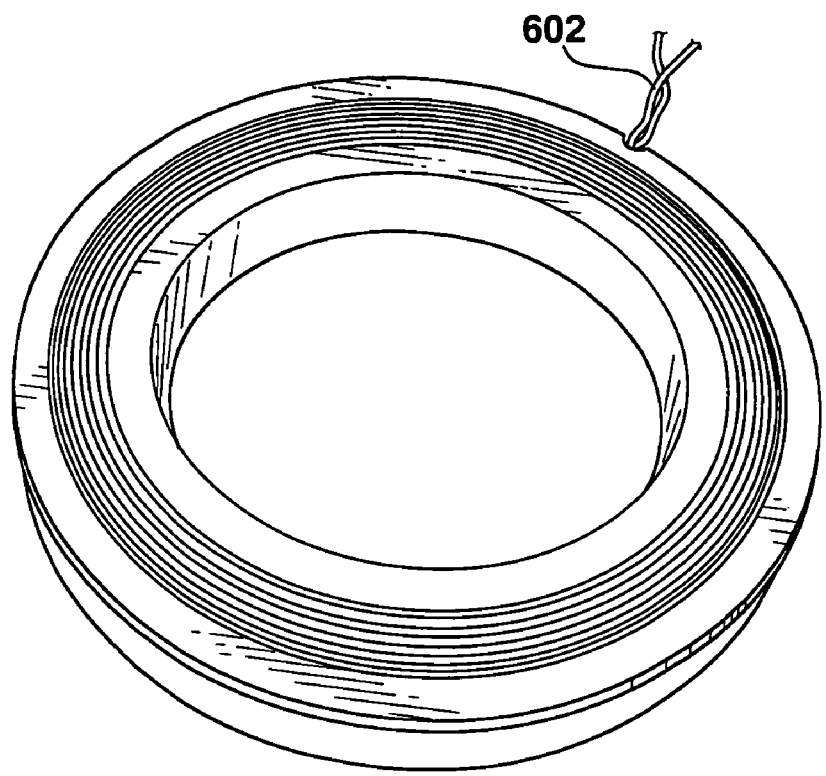
Figure 7A:
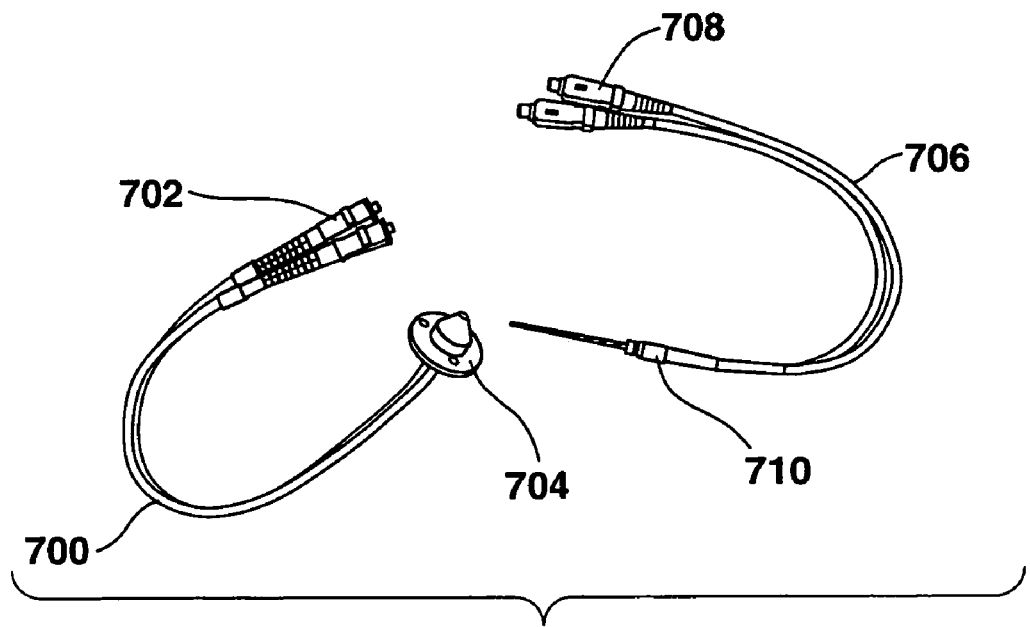
FIGS. 7(*a*)–(*f*) show optical fiber components that can be used with the system of FIG. 1.
Figure 7B:
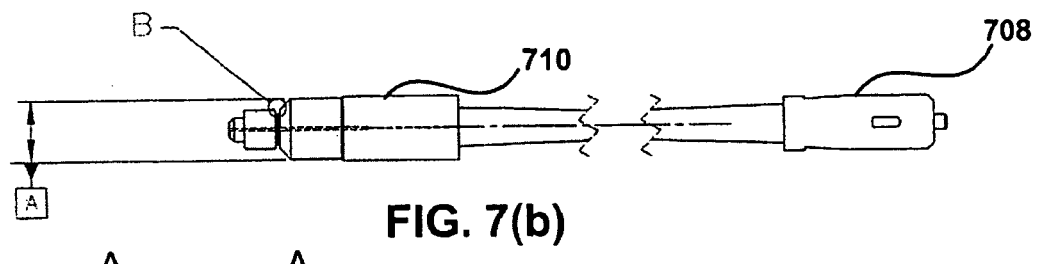
Figure 7C:
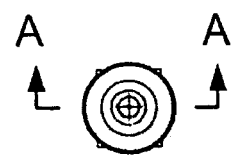
Figure 7D:
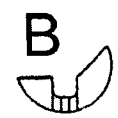
Figure 7E:
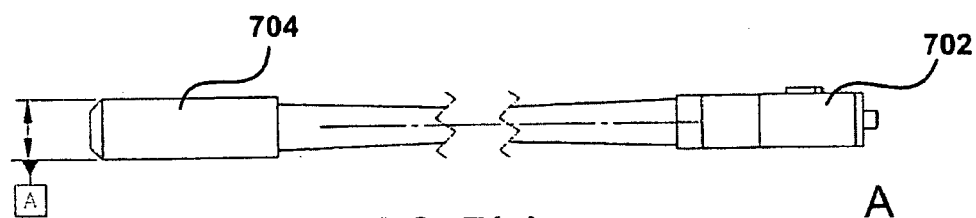
Figure 7F:
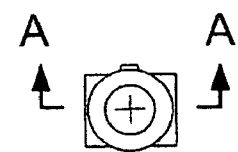

Other radial symmetric arrangements of a rotary transformer can be used to provide similar coupling and isolation, such as the arrangement 500 shown in FIG. 5. As shown in the figure, the substantially parallel ring cores can be replaced with concentric cylinders 502, 504 separated by a tubular gap 510. One of the wire coils can be positioned in the groove 506, or simply on the outer surface, of a central cylinder 502. A matching coil can be mounted in a groove 508, or simply on the inside, of a matching hollow cylinder 504, such as a ferrite tube. The central cylinder can be mounted inside the tube, with a substantially common central axis for the two cylinders, such that power can be transferred between the inner cylinder 502 and the outer tube 504, thereby achieving the same result as for the arrangement of FIG. 4 to transfer power between the power electronics 516, 518. An optical fiber again can be used to transfer information between an optical transceiver 512 and a data interface 514. Other embodiments can use other arrangements, such as the use of standard pot-cores to house the power transformer coils and a simple LED emitter and detector mounted in the center of the pot core to enable one-way transfer of data.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. A system for transmitting power and an optical signal between components of a surveying instrument, comprising:
    a first ring core having a first central axis and including a first coil disposed in a first surface of the first ring core, the first coil operable to be connected to a first component in order to receive power from the first component;
    a second ring core positioned substantially parallel to the first ring core and having a second central axis aligned with the first central axis, the second ring core including a second coil disposed in a second surface adjacent the first surface and positioned a distance from the first coil such that power can be passed from the first coil to the second coil, the second coil operable to be connected to a second component in order to transmit current to the second component, the second ring core further being operable to rotate relative to the first ring transformer about the second central axis; and
    an optical data link positioned in a central opening in each of the first and second ring cores, the optical data link operable to pass an optical signal between third and forth components of the surveying instrument, the third and fourth components being rotatable with respect to each other.

2. A system according to claim 1, wherein:
    the second and fourth component comprise the same component.

3. A system according to claim 1, wherein:
    at least one of the first and second ring cores is a ferrite core.

4. A system according to claim 1, wherein:
at least one of the first and second ring cores includes a groove in the respective one of the first and second surfaces for housing a respective portion of the first and second coils.

5. A system according to claim 1, wherein:
at least one of the first and second ring core includes a channel allowing a respective one of the first and second coils to connect to a respective one of the first and second components.

6. A system according to claim 1, wherein:
the optical data link is positioned substantially along the first and second central axes.

7. A system according to claim 1, wherein:
the optical data link includes first and second optical fiber portions, the first and second optical fiber portions being rotatably connected in order to allow for rotation of at least one of the first and second fiber portions while maintaining a common optical path between the first and second optical fiber portions.

8. A system according to claim 1, wherein:
the optical data link includes first and second optical fiber portions in optical communication, the first and second optical fiber portions having adjacent ends allowing an optical signal to pass along a common optical path formed by the first and second optical fiber portions.

9. A system according to claim 1, wherein:
at least one of the first and second components is an optical transceiver.

10. A system for transmitting power and an optical signal between components of a surveying instrument, comprising:
a first electromagnetic cylinder having a first central axis and including a first coil disposed about an outer cylindrical surface of the first electromagnetic cylinder, the first coil operable to be connected to a first component in order to receive power from the first component;
a second electromagnetic cylinder positioned substantially concentric to, and outside of, the first electromagnetic cylinder and having a second central axis aligned with the first central axis, the second electromagnetic cylinder including a second coil disposed about an inner cylindrical surface adjacent the outer cylindrical surface and positioned a distance from the first coil such that power can be passed from the first coil to the second coil, the second coil operable to be connected to a second component in order to transmit power to the second component, the second electromagnetic cylinder being further operable to rotate relative to the first electromagnetic cylinder about the second central axis; and
an optical data link positioned in a central opening in each of the first and second electromagnetic cylinders, the optical data link operable to pass an optical signal between third and forth components of the surveying instrument, the third and fourth components being rotatable with respect to each other.

11. A system according to claim 10, wherein:
at least one of the first and second electromagnetic cylinders includes a groove in the respective one of the outer and inner cylindrical surfaces for housing a respective portion of the first and second coils.

12. A system according to claim 10, wherein:
the optical data link is positioned substantially along the first and second central axes.

13. A system according to claim 10, wherein:
the optical data link includes first and second optical fiber portions, the first and second optical fiber portions being rotatably connected in order to allow for rotation of at least one of the first and second fiber portions while maintaining a common optical path between the first and second optical fiber portions.

14. A system according to claim 10, wherein:
the optical data link includes first and second optical fiber portions in optical communication, the first and second optical fiber portions having adjacent ends allowing an optical signal to pass along a common optical path formed by the first and second optical fiber portions.

* * * * *